(12) United States Patent
Kunz

(10) Patent No.: US 7,252,660 B2
(45) Date of Patent: Aug. 7, 2007

(54) MULTIFUNCTIONAL INSTRUMENT FOR USE IN MICROINVASIVE SURGERY

(76) Inventor: Reiner Kunz, Tucholskyhoene 4, 14532 Kleinmachnow (DE)

( * ) Notice: Subject to any disclaimer, the term of this patent is extended or adjusted under 35 U.S.C. 154(b) by 444 days.

(21) Appl. No.: 10/489,868

(22) PCT Filed: Sep. 24, 2002

(86) PCT No.: PCT/DE02/03581

§ 371 (c)(1), (2), (4) Date: Mar. 24, 2004

(87) PCT Pub. No.: WO03/026511

PCT Pub. Date: Apr. 3, 2003

(65) Prior Publication Data

US 2004/0249366 A1    Dec. 9, 2004

(30) Foreign Application Priority Data

Sep. 25, 2001    (DE) ................................ 101 47 145

(51) Int. Cl.
*A61B 17/00*    (2006.01)

(52) U.S. Cl. ............................................................ 606/1

(58) Field of Classification Search .................... 606/1, 606/32, 41; 604/19, 43
See application file for complete search history.

(56) References Cited

U.S. PATENT DOCUMENTS

| | | | |
|---|---|---|---|
| 5,350,355 A | 9/1994 | Sklar | |
| 5,368,015 A | 11/1994 | Wilk | |
| 5,755,713 A * | 5/1998 | Bilof et al. ..................... | 606/1 |
| 5,766,169 A | 6/1998 | Fritzsch et al. | |
| 5,776,092 A | 7/1998 | Farin | |
| 5,871,495 A | 2/1999 | Mueller | |
| 5,954,731 A * | 9/1999 | Yoon ............................. | 606/144 |
| 5,980,469 A | 11/1999 | Burbank | |
| 6,497,704 B2 * | 12/2002 | Ein-Gal ......................... | 606/41 |
| 6,626,902 B1 * | 9/2003 | Kucharczyk et al. ......... | 606/41 |
| 6,837,883 B2 * | 1/2005 | Moll et al. ..................... | 606/1 |

FOREIGN PATENT DOCUMENTS

| | | |
|---|---|---|
| AT | 38782 | 3/1989 |
| DE | 4213426 | 10/1992 |
| DE | 19537897 | 3/1997 |
| EP | 0692224 | 1/1996 |
| WO | WO99/22650 | 5/1999 |

* cited by examiner

*Primary Examiner*—Michael Peffley
*Assistant Examiner*—Pete Vrettakos
(74) *Attorney, Agent, or Firm*—Dennison, Schultz & MacDonald

(57) ABSTRACT

A multifunctional instrument for use in microinvasive surgery includes an operator hand grip, a multi-lumen tube fastened on the operator hand grip, at least two guide channels coaxially configured inside the tube, and surgical instruments that are displaceably and rotationally disposed in the guide channels. The instrument also includes a shaft at whose distal end one surgical working element each is disposed. The instruments can be displaced between a rest position, in which the respective working element is retracted into the tube, and a working position, in which the respective working element projects from the distal end of the tube. The instruments can be displaced into and out of the working position by means of a motor and at least one of the instruments can be rotated in its working position by means of a motor. The instrument can be controlled by means of an electronic control that controls at least the motor-driven displacement motions and rotational motions of the surgical instruments and the tube.

23 Claims, 6 Drawing Sheets

DISPLACE CLIP

ROTATE INDIVIDUAL INSTRUMENT

ROTATE CLIP

MULTIFUNCTIONAL INSTRUMENT FOR USE IN MICROINVASIVE SURGERY

Figure 1:
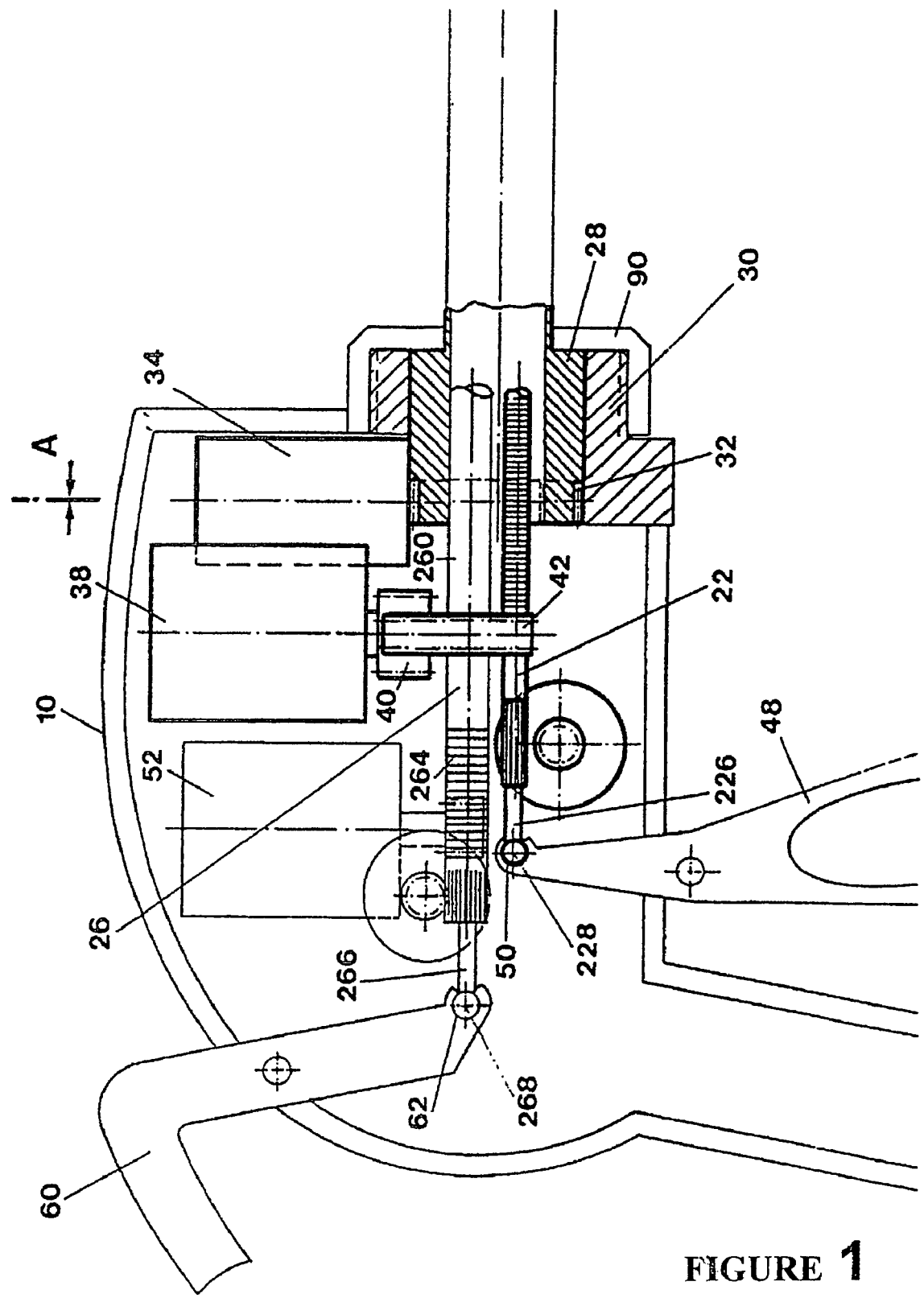

The invention relates to a multifunctional instrument for use in microinvasive surgery having an operator hand grip, a multi-lumen tube attached to the operator hand grip, at least two guide channels formed coaxially in the tube, and surgical instruments which are displaceably and rotatably mounted in the guide channels and comprise a shaft, on whose distal end is disposed in each case a surgical working element, wherein the instruments can be displaced between a non-operative position, in which the respective working element is retracted into the tube, and a working position, in which the respective working element projects from the distal end of the tube.

In areas of medicine in which operations are performed (surgery, gynaecology, urology, neurosurgery etc.), there is a continuous attempt to reduce the operative trauma, i.e. the damage to the patient caused by the operation itself. One way of reducing the operative trauma is to minimise the operative access path.

Operations on the abdominal area by laparoscopy were first performed over a decade ago. In this case, in addition to a lens system which is coupled to a video chain, various individual instruments required to perform the operation are introduced via several separate access paths into the abdominal cavity. The actual procedure in the abdominal area is performed in principle without modification according to an operation where a classic incision is performed on the skin, so that the difference in principle is that the classic procedure of gaining access by separating the abdominal wall is omitted.

The stress reactions of the organism during and after the operation are substantially reduced with a minimally invasive access path. As a result, the operation is less painful, the patient can be mobilized more quickly, can be discharged from hospital earlier and is able to resume his/her activities and employment within a shorter period of time.

In general, the laparoscopic operational instruments available on the market combine a maximum of 2 functions, i.e. the typical surgical procedure, namely exposing a structure, closing it (e.g. with clips), cutting through the structure and exposing further structures is associated with using several different operational instruments. Measurements have shown that changing an instrument in minimally invasive operations takes approximately 40 seconds from the moment a decision to change the instrument is made to the moment the new instrument is positioned in the area where the operation is being performed. A reduction in this time interval can lead to a considerable reduction in the overall time of the operation. If the various necessary instrument functions are performed with one device, it could even be the case that a theatre sister or assistant does not have to be involved for long periods during the operation.

EP 0 692 224 B1 discloses a multifunctional instrument for microinvasive surgery of the generic type stated in the introduction. One of the problems associated with the multifunctional device disclosed therein is that active manual energy is required to select the surgical instruments and to rotate the tube. As a consequence, the multifunctional device could fall apart when changing an instrument. Moreover, the user's other hand is often also required when changing an instrument. The procedures of pulling back, selecting and then pushing forward the surgical instrument must also be controlled by the surgeon using sensory means.

A further problem of the known multifunctional instrument is that when the respectively used surgical instrument is guided back by means of resilient force, a reaction force or reaction pulse is exerted upon the multifunctional instrument. Although this undesired reaction pulse can be reduced by corresponding damping members, such damping members, on the other hand, add to the weight of the multifunctional device which essentially should be kept as light as possible to enable effective handling. It should also be noted that in this case the surgeon is also required to use active manual energy in order to move the surgical instruments to the working position, in which the said spring is stressed.

Essentially, it is the object of the invention to provide a multifunctional instrument for microinvasive surgery which renders it possible to change an instrument conveniently and quickly and supports the surgeon in this task, wherein at the same time any undesired side effects, such as the multifunctional instrument falling apart, and any reaction pulses are obviated.

In accordance with the invention, this object is essentially achieved by virtue of the fact that the instruments can be displaced into and out of the working position by means of a motor, that at least one of the instruments can be rotated in its working position by means of a motor and that an electronic control is provided to control at least the motor-driven displacement movements and rotational movements.

In a preferred development of the invention, it is provided that the multi-lumen tube is rotatably mounted on the operator hand grip and can likewise be rotated by means of a motor, wherein the rotational movement can be controlled by means of the electronic control.

By reason of the fact that the surgical instruments are extended and retracted by means of a motor and that the multi-lumen tube is rotated by means of a motor to select the surgical instrument desired in each case, the surgeon is no longer required to perform any corresponding manual movement sequences, the multifunctional device cannot fall apart when changing an instrument and any reaction pulses caused by return springs can be completely obviated in practical terms by actuating the motors accordingly. Furthermore, the multifunctional device in accordance with the invention permits genuine one-handed operation.

The commands for the electronic control can be input via actuating elements, such as e.g. keys/buttons, which are disposed on the operator hand grip. Alternatively, verbal commands can be input by a corresponding voice-control facility. In this case, the commands to be processed by the control should at least include the following: move the surgical instruments to the non-operative position or the working position or rotate the surgical instruments. It can also be advantageous if the commands are input by voice-controlled means or by actuating elements.

The motor-drive means are preferably electromotors, e.g. micro-transmission motors which are disposed in the operator hand grip of the multifunctional instrument. In a preferred development of the invention, it is provided that the electromotors allocated to the surgical instruments can be coupled selectively to the surgical instrument, which is to be selected in each case, by way of coupling elements which are connected between the respective instrument and the allocated electromotor, wherein this selective coupling is preferably accomplished by a relative movement between the instrument and the allocated electromotor or allocated coupling element. A particularly convenient construction is achieved if the electromotors are fixedly disposed in the hand grip and the selective coupling is accomplished substantially by a suitable rotation of the tube, wherein depending upon the angular position of the tube, different surgical instruments are coupled to the respectively allocated electromotors for an axial movement or rotational movement.

Force is transmitted from the drive motors to the surgical instruments preferably by way of suitable gear wheels like pinions, worm wheels etc. In accordance with a further advantageous feature of the invention, to absorb the drive force a proximal end portion of the shaft of each instrument, which when inserted into the tube projects from the proximal end of the tube, comprises suitable toothing arrangements. In particular, the shaft comprises at least one of the surgical instruments, preferably all surgical instruments, a first toothed portion for displacing the instrument in an axial direction and a second toothed portion for rotating the surgical instrument.

In accordance with a further advantageous development of the invention, the shaft at least of one of the surgical instruments comprises at its proximal end a coupling element for engagement with an actuating element for manually actuating the instrument. As soon as the surgical instrument selected in each case is coupled via the coupling element to the actuating element and has been displaced to its working position by means of the allocated electromotor, it can then be operated manually by the surgeon; this type of manual actuation is provided for surgical instruments, in which tactile feedback is required or desired, e.g. for scissors or clamp applicators, whereas e.g. for clip applicators tactile feedback is not necessarily required and therefore it is also possible to provide a motor-driven working stroke.

Accordingly, in a further advantageous embodiment of the invention it is provided that at least two of the surgical instruments, e.g. scissors and clamp applicator, have a short working stroke with tactile feedback and, after being moved by a motor to their working position, can be actuated manually and that at least one of the surgical instruments, e.g. the clip applicator with a long working stroke can be actuated manually or by means of a motor after being displaced to its working position by means of a motor.

In order to ensure that the multifunctional instrument can be utilised in the broadest possible way, the tube preferably comprises guide channels with a different diameter, as e.g. clip applicators require a larger diameter than scissors. The tube preferably comprises at least three guide channels, in particular two guide channels having a first diameter and one guide channel having a second diameter which is larger than the first diameter, wherein the first diameter can be about 3 mm and the second diameter about 5 mm.

In a preferred development of the invention, it is provided that the tube comprises at least one additional channel which serves as a suction or rinsing channel. Preferably, the tube comprises two additional channels which are disposed in particular adjacent to the guide channel having the larger diameter and, in order to utilise the available cross-section in an optimum manner, comprise an approximately triangular-shaped cross-section. In an expedient manner, the arrangement of the guide channels can be such that the angular spacing between the two guide channels with the smaller diameter is 90° as seen in relation to the longitudinal middle axis of the tube, and the angular spacing between the guide channels with the smaller diameter on the one hand and the guide channel with the larger diameter on the other hand is 135° in each case.

In order for the fluid, which is guided in the additional channel, to be supplied into and carried off from the additional channel, it is provided in accordance with a further advantageous feature of the invention that each of the additional channels comprises on the proximal end portion of the tube an outlet which extends radially outwards and is connected to a suction/rinsing connection which is attached to the operator hand grip. It is also provided that in the contact region between the tube and the component which surrounds the tube in a sealing manner in the region of the outlet(s), there is provided a space which is connected on the one hand to the outlet and on the other hand to the suction/rinsing connection, extends in the circumferential direction of the tube and which ensures that the fluid connection between the additional channel and the suction/rinsing connection remains intact even when the tube is rotated relative to the component.

Further advantageous features of the invention are given in the remaining subordinate claims and in the description hereinunder, in which several exemplified embodiments of the invention are explained in detail with reference to the drawing. In the semi-schematic or schematic illustrations of the drawings, FIG. 1 shows a partially cut partial side view of a multifunctional instrument in accordance with the invention, FIG. 2 shows a partially cut view of the multifunctional instrument as shown in FIG. 1.

Figure 2:
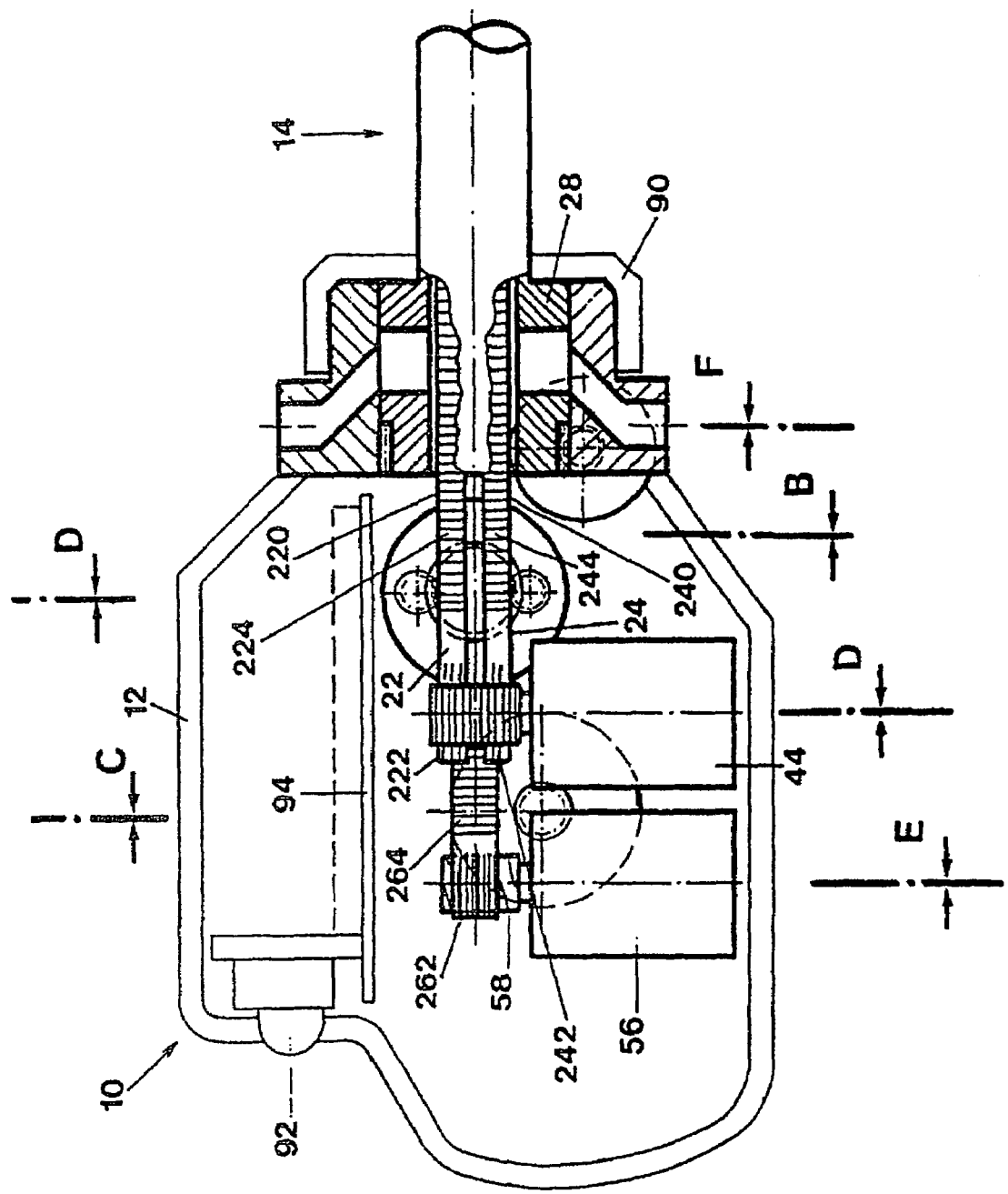
Figure 3:
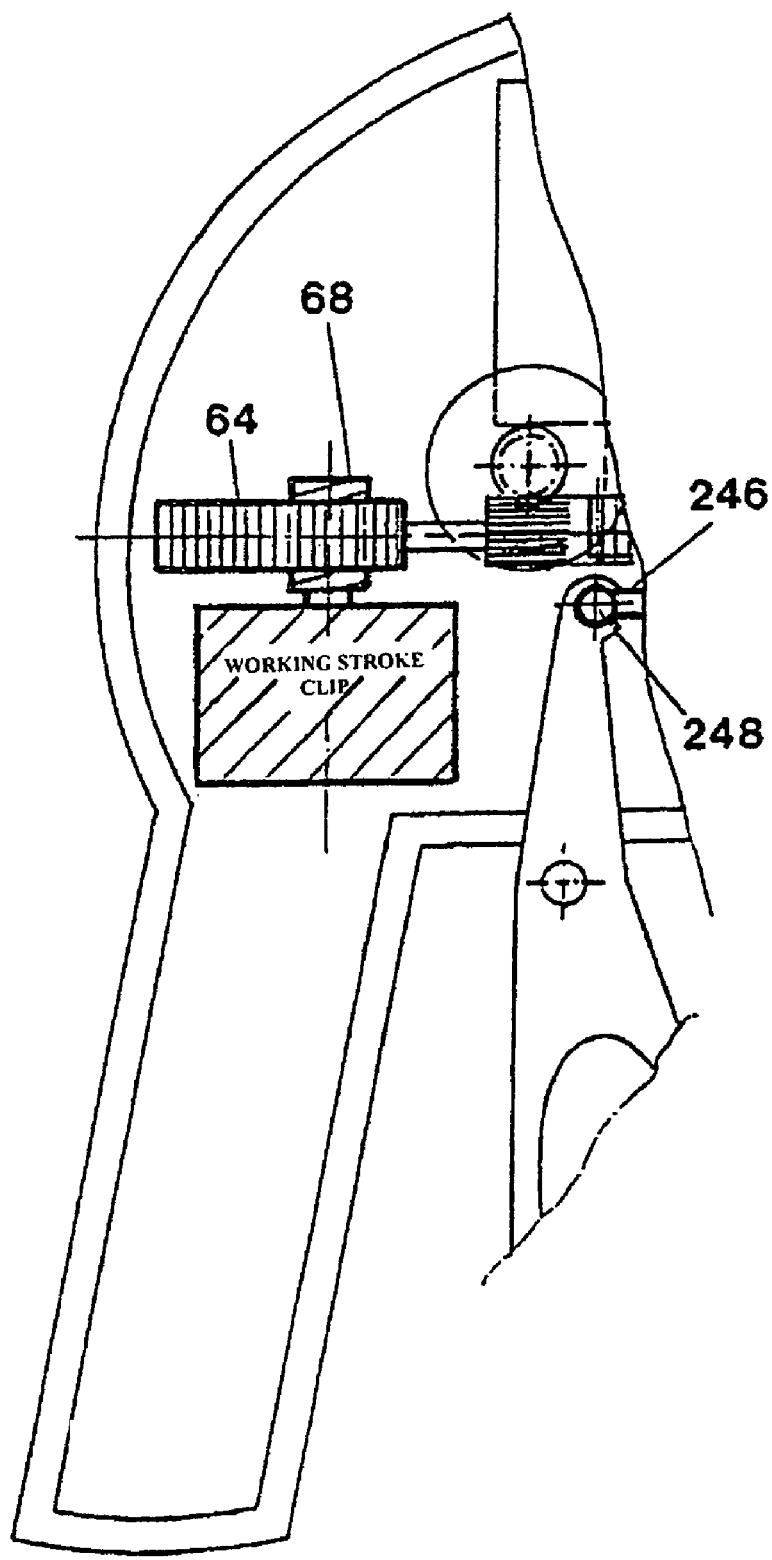
Figure 4:
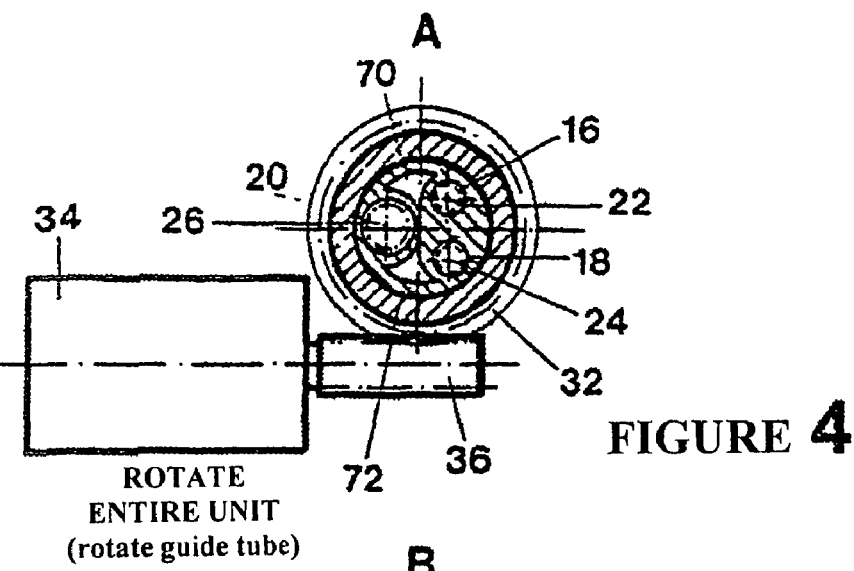
Figure 5:
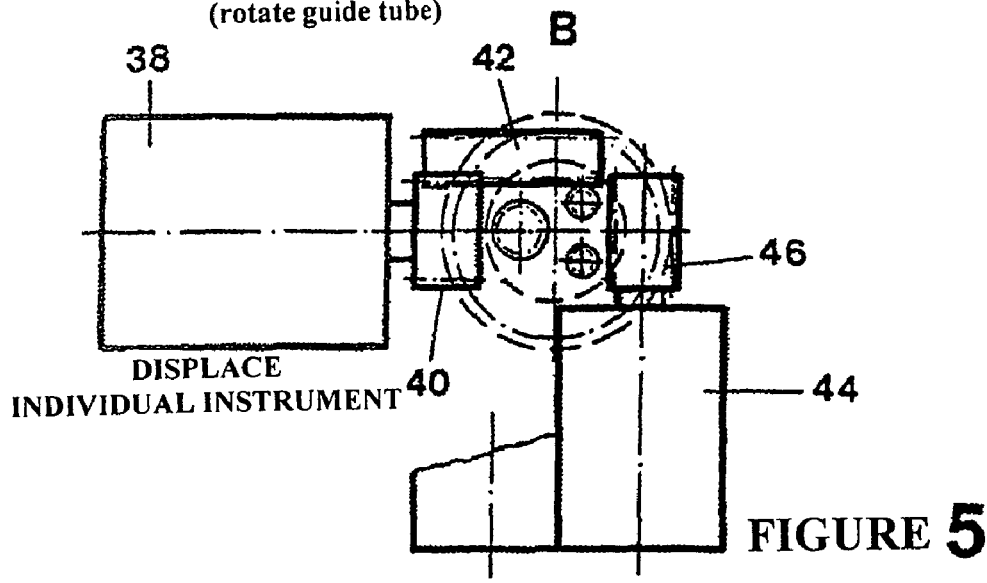
Figure 6:
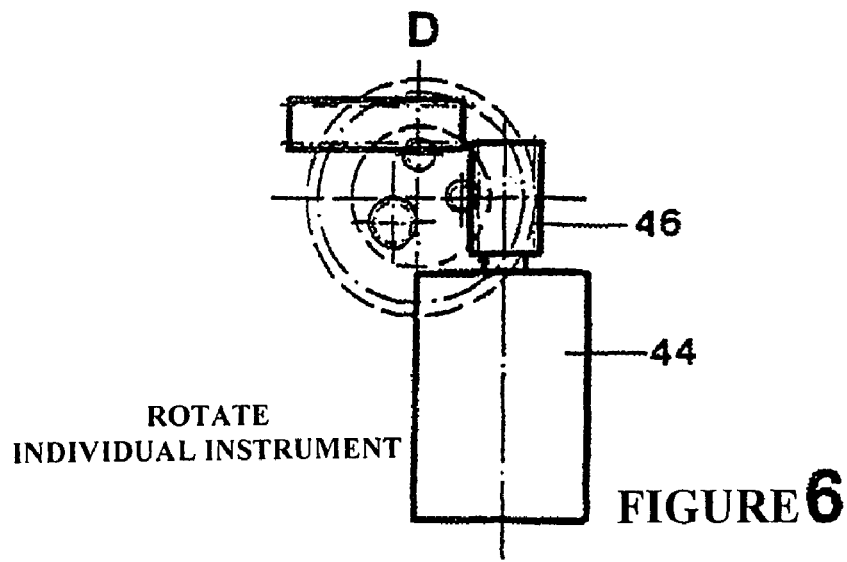
Figure 9:
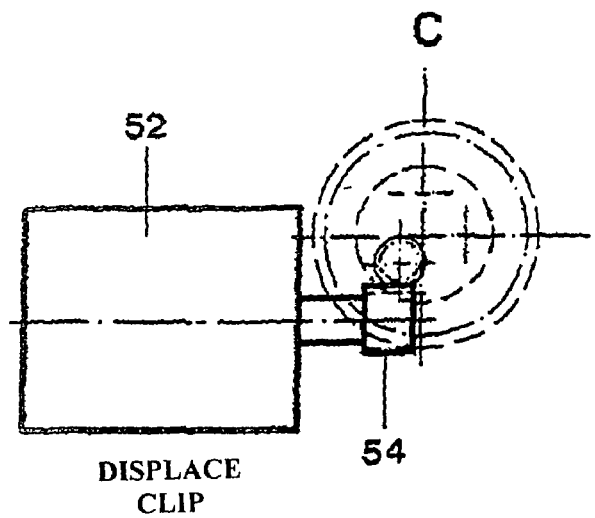
Figure 7:
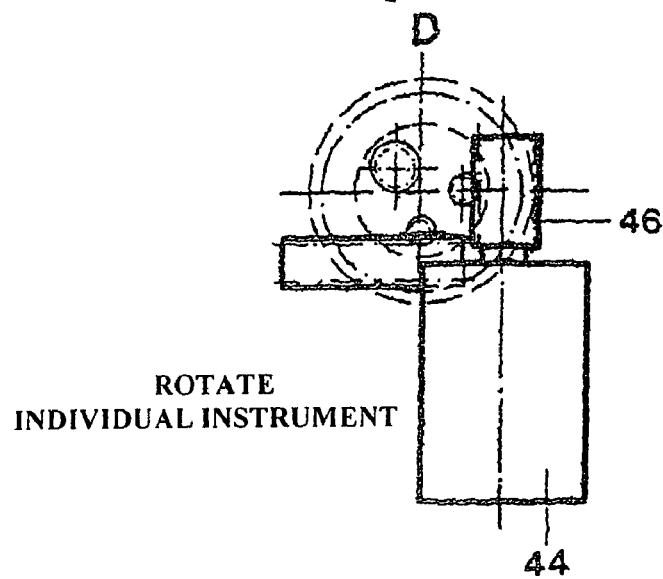
Figure 8:
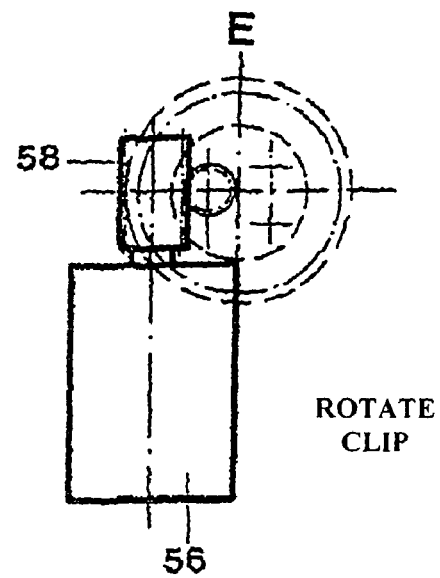
Figure 10:
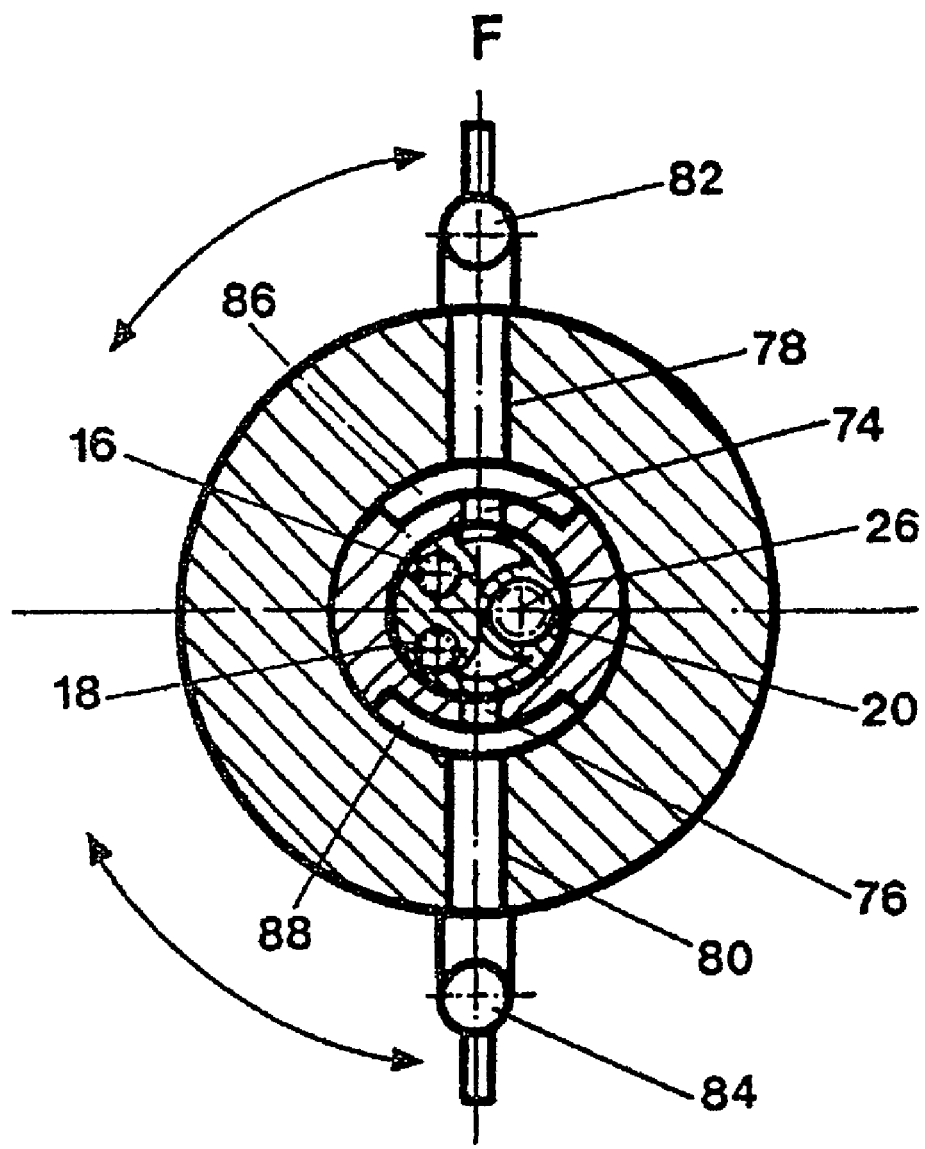

FIG. 3 shows a partial view of a modified exemplified embodiment of a multifunctional instrument as shown in FIG. 1, FIG. 4 shows a partially cut partial view illustrating the drive for the tube, FIG. 5 shows a partial view illustrating the functional position, in which a first surgical instrument can be displaced, FIG. 6 shows a partial view illustrating the functional position, in which a second surgical instrument can be rotated, FIG. 7 shows a partial view illustrating the functional position, in which the first surgical instrument can be rotated, FIG. 8 shows a partial view illustrating the functional position, in which a third surgical instrument can be rotated, FIG. 9 shows a partial view illustrating the functional position, in which the third surgical instrument can be displaced, and FIG. 10 shows a radial section of the proximal end of the tube.

The multifunctional instrument in accordance with the invention comprises a pistol-shaped, angle-bent operator hand grip 10 having a casing 12 and comprises a multi-lumen tube 14 which is detachably mounted on the operator hand grip 10, is mounted so as to be able to rotate by way of bearing shells or a sleeve bearing and has three guide channels 16, 18, 20 which are formed coaxially with respect to the tube axis and in which surgical instruments 22, 24, 26 are displaceably mounted in a longitudinal direction and in addition are also rotatably mounted. Each of the surgical instruments 22, 24, 26 comprises on its distal end, not illustrated here, an operation tool such as scissors, a clamp applicator or a clip applicator which is connected to a shaft 220, 240 and 260 respectively. Each shaft comprises on its proximal end portion a first toothed portion 222, 242, 262 and a second toothed portion 224, 244, 264 which adjoins the first toothed portion in the direction towards the distal end. In the case of the surgical instruments which are inserted into the tube 14 and are in the non-operative position, the shafts of the surgical instruments project with their proximal end portion from the proximal end of the tube 14, so that the toothed portions of the shafts can be brought selectively into engagement with drive elements such that the desired one of the surgical instruments 22, 24, 26 is able to advance from its non-operative position, in which the working tool is retracted in the allocated guide channel, to a working position, in which the selected surgical working tool projects from the distal end of the tube 14 and in this position can then be actuated manually or by a motor or can also be rotated by a motor as required.

The tube 14 comprises on its proximal end a bearing portion 28 having a diameter which is larger than the remainder of the tube and which is rotatably mounted in a bearing block 30 which is provided on the distal end of the, overall, approximately pistol-shaped operator hand grip 10. Formed on the proximal end of the bearing block 30 is a toothing arrangement 32 which extends over the periphery thereof. An electromotor 34 which is disposed in the casing 12 of the operator hand grip 10 drivingly engages with a motor pinion 36, which is attached to its output shaft, into the toothing arrangement 32 of the bearing portion 28 of the tube 14, whereby the tube 14 can be rotated by means of the electromotor 34, cf. in particular FIGS. 1 and 4.

In order to displace the surgical instruments 22, 24 which are e.g. scissors, a clamp applicator or a contact hook, an electromotor 38 is provided which is secured in the casing 12 and cooperates via a motor pinion 40 and an intermediate pinion 42 in a driving manner with the radial toothing arrangement of the second toothed portion 224 or 244 of the respective shaft 220 or 240, cf. in particular FIGS. 1 and 5. The intermediate pinion 42 of the electromotor 38 comes into engagement with the second toothed portion of the respective shaft by virtue of the fact that the tube is rotated by means of the electromotor 34 to the corresponding angular position. Starting from a basic position of the tube or surgical instruments, as shown in FIG. 5, the surgical instruments pivot into the toothing arrangement of the intermediate pinion 42 by reason of the corresponding rotation of the tube as shown in FIGS. 6 and 7.

The surgical instrument which is in engagement with the intermediate pinion 42 can thus be displaced in an axial direction via the motor 38. As soon as the selected surgical instrument has been extended to the working position, a rotation of the tube 14 through 90° moves said instrument with its end toothing arrangement in the first toothed portion 222 or 242 into engagement with a motor pinion 46 which is attached to the output shaft of an electromotor 44 secured in the casing 12 of the operator hand grip 10. By means of the motor 44, it is thus possible to rotate the respectively selected surgical instrument 22 or 24 as required. Formed in each case on the proximal end of the shaft 220, 240 of the surgical instrument 22, 24 is a rod 226, 246 which is coaxial with the shaft and whose proximal end has a coupling ball 228, 248 integrally formed thereon. An operator pivot lever 48 which is pivotally mounted on the casing and of which one lever arm projects into the casing 12 comprises at the end of this lever arm a receiving orifice 50, whose shape is tailored to suit the shape of the coupling ball 228, 248 and which is able to receive the coupling ball 228, 248 in a lockable and releasable manner. In the position illustrated in FIGS. 6 and 7, the selected surgical instrument 22 or 24 is moved rearwards until its coupling ball 228, 248 enters and latches into the receiving orifice 50 of the operator pivot lever 48. It is then possible to actuate the working tool manually in a direct manner which is expedient in particular for such surgical instruments which require tactile feedback, such as e.g. scissors.

The surgical instrument 26 which can be provided on its distal end, for example, with a clip applicator can be displaced by means of an electromotor 52 which is fixedly disposed in the casing 12 of the operator hand grip 10 and, by way of a motor pinion 54 which is attached to its output shaft, can be brought in a driving manner into engagement with the radial toothing arrangement of the second toothed portion 264 of the shaft 260 of the surgical instrument 26 with the tube 14 in a corresponding angular position, cf. FIGS. 1 and 9. With the tube 14 in a corresponding position, a further electromotor 56 which is secured in the casing is in driving engagement, by way of a motor pinion 58 attached to its output shaft, with the end toothing arrangement of the first toothed portion 262 of the shaft 260 of the surgical instrument 26 and thus permits rotation of the surgical instrument 26, cf. FIGS. 2 and 8. The surgical instrument 26 is pivoted into the drive position as shown in FIGS. 8 and 9 by correspondingly rotating the tube 14, as described earlier.

In accordance with the surgical instruments 22 and 24, the surgical instrument 26 also comprises on its proximal end a rod 266 whose proximal end has a coupling ball 268 formed thereon which can be latched into a receiving orifice 62 of a further operator pivot lever 60 which is pivotally mounted on the casing 12 and comprises the receiving orifice 62 on its pivot arm which projects into the interior of the casing 12. When the surgical instrument 26 is in the working position, the coupling ball 268 is latched in the receiving orifice 62 and the surgical instrument 26 can thus be operated manually in a direct manner in the same way as the surgical instruments 22 and 24.

Instruments which do not require any tactile feedback about tissue constitution but must merely move back and forth as the working stroke, e.g. instruments for placing a clip, can also be actuated by means of a motor, cf. FIG. 3 which in this respect illustrates an alternative embodiment. Provided in this case instead of the coupling ball 268 is a toothed rod 64 which has a radial toothing arrangement and, when the surgical instrument 26 is in the working position, is in driving engagement with a motor pinion 68 of an electromotor 66 secured in the casing 12.

In the case of the illustrated exemplified embodiment, the diameter of the guide channels 16, 18 which receive the surgical instruments 22, 24 is 3 mm, wherein the surgical instruments 22, 24 have an approximately equally large working stroke. In the case of this exemplified embodiment, the diameter of the guide channel 20 which receives the surgical instrument 26 is 5 mm and this surgical instrument can have a shorter or longer working stroke than the surgical instruments.

The two guide channels 16, 18 are disposed at an angular spacing of 90° in relation to the middle axis of the tube and the angular spacing of the guide channel 20 with respect to the guide channel 16 and the guide channel 18 is 135° in each case. The spaces located between the guide channel 16 and the guide channel 20 and the guide channel 18 and the guide channel 20 are utilised to form further channels 70, 72 which are used in particular as rinsing and suction channels. In order to make optimum usage of space, the channels 70 have an approximately triangular cross-section with curved side surfaces corresponding to the adjacent walls.

The channels 70, 72 open towards the distal end of the tube in an axial direction and comprise, on the proximal end of the tube 14 in the region of the bearing portion 28, a respective radial outlet 74, 76 which runs onto a respective suction/rinsing connection channel 78, 80 which is formed in the bearing block 30 and on which the suction/rinsing connections 82, 84 are attached. Furthermore, the outer end of each radial outlet 74, 76 is adjoined in each case by a space 86, 88 which extends in the circumferential direction of the tube on both sides of the outlet over an angular range of e.g. 90° in total and is open towards the outside. In this manner, even when the tube 14 is rotated relative to the operator hand grip 10, the connection between the respective radial outlet of the channel and the allocated suction/rinsing connection remains intact.

As already mentioned, the synthetic material tube 14 on the operator hand grip 10 is detachable and can be inserted with its bearing portion 28 in an axial direction into the bearing block 30 of the operator hand grip 10 and can be fixed in its functional position by means of a union nut 90 which is secured by means of a captive ring. On the one hand, the ability to detach the tube 14 from the operator hand grip 10 makes it easier to clean the tube 14 and on the other hand makes it easy to fit the tube 14 from the rear.

Unless operated using the operator pivot levers 48 and 60, the multifunctional instrument is operated by means of an electronic control, not illustrated, which can be disposed outside the operator hand grip 10 and can be connected thereto by a cable. The control commands are received by the electronic control either via a key pad which is disposed on the casing 12 of the operator hand grip 10 and which is indicated in FIG. 2 by the reference numeral 92, or via a voice-input control. In particular, the following control commands are provided: instrument 22 forwards and back, instrument 24 forwards and back, instrument 26 forwards and back, rotate instrument in working position right or left, working stroke of instrument 26 in working position (cf. FIG. 3).

In the case of the exemplified embodiment as shown in FIG. 2, the actual electronic control is located inside the casing 12 and is indicated by the printed circuit board 94. In the case of all of the embodiments, sensors, not illustrated in detail, detect the positions of the respective instruments. This positional data is processed in the electronic control and, in accordance with the control commands input via the key pad or voice-input facility, the corresponding electromotors are then actuated. In the case of a voice-control facility, this is performed on an external computer which is then able to communicate the corresponding commands to the electronic control located in the casing 10 or communicate them directly to the electromotors.

In order to perform coagulation, the tube 14 must be insulated. For this very reason the tube 14 is manufactured from synthetic material. One of the surgical instruments 22, 24 is used for coagulation. The voltage required to achieve coagulation is supplied by contacting the peripheral surface of the instrument 22, 24 or else the respective coupling ball 228, 248. The unipolar connection is established on the casing 12 or on the operator pivot lever 48.

The multifunctional instrument in accordance with the invention thus renders it possible to use three different surgical instruments within the tube 14, without the surgeon having to pull the tube 14 out of the trocar for this purpose. The surgical instruments are moved to the working position by suitable actuating elements on the operator hand grip 10 or via a voice-control facility, the instruments are optionally coupled to the operator pivot levers for manual actuation or are actuated by means of a motor, if a motor-driven working stroke is to be performed. The surgical instruments required for various steps of an operation are thus kept available at the operation site so that they can be interchanged simultaneously and rapidly.

The multifunctional instrument in accordance with the invention enables operation time to be saved. Further potential savings are achieved by the fact that an instrument nurse is not required for lengthy parts of the operation, as no instruments need to be changed, as long as the multifunctional instrument in accordance with the invention is able to provide all instrument functions at the operation site, e.g. in the abdominal cavity.

A further substantial advantage of the multifunctional instrument in accordance with the invention is that in contrast to prior art multifunctional instruments it can be conveniently adapted to a medical robot, as in the foreseeable future the most varied operations such as coronary blood vessel operations or operations on the spinal column and joints will increasingly not be performed directly by the surgeon himself but rather by the intermediary of robot arms (telemedicine-robotics). A multifunctional instrument in accordance with the present invention, positioned between the robot arm and operation site, increases usage capability, as in this case the individual robot arm is no longer fixed to a single instrument but can be equipped with variable functions.

A further advantage of the multifunctional instrument in accordance with the invention is achieved due to the circumstance that there is no longer a need for a theatre nurse or theatre assistant who passes the instruments required in each instance and any possible communication errors, e.g. passing the wrong instruments, which could disrupt the operational procedure or jeopardise the outcome of the operation are omitted.

The following is a brief summary of the approach taken with the multifunctional instrument in accordance with the invention:

The reusable instruments or parts of instruments from previous operations are sterilised. A selection is made preoperatively of the required instruments to be used, such as e.g. scissors, clamping forceps, clip etc. The selected instruments are inserted into the tube, which has been detached from the operator hand grip, from the rear into the respective guide channels. The tube is placed onto the operator hand grip and secured by means of the union nut 90. The individual instruments are automatically retracted to and positioned in their non-operative position within the tube. External (non-sterile) auxiliary devices are coupled where appropriate to the operator hand grip. Using the keys/buttons located on the casing or by means of a voice-control facility, a selection is made intraoperatively of the surgical instrument which is then moved automatically to the working position and is coupled to the operator pivot lever. If a change of instrument is required and the corresponding instrument is actuated by the push of a button or by voice-control, then the hitherto used instrument is automatically moved to its non-operative position, the selected next instrument is automatically selected and moved automatically to its working position. The instrument in the working position can be rotated at any time. After the operation has been completed and the last used surgical instrument has been moved to its non-operative position, the tube is removed from the body of the patient, is detached from the operator hand grip and is cleaned along with the surgical instruments which have been used.

Numerous modifications can be made by the person skilled in the art. For example, the surgical instruments can be coupled electrically, pneumatically or hydraulically to the energy carrier in the hand grip or externally in the non-sterile operation area. If the surgical tools do not have to be rotated, it is possible in this respect to dispense with the corresponding motor-driven drive means. The individual elements can also be rotated by motor in that the tube is rotated as a whole.

LIST OF REFERENCE NUMERALS 10 operator hand grip
12 casing
14 tube
16 guide channel
18 guide channel
20 guide channel
22 surgical instrument
220 shaft
222 $1^{st}$ toothed portion
224 $2^{nd}$ toothed portion
226 rod
228 coupling ball
24 surgical instrument
240 shaft
242 $1^{st}$ toothed portion
244 $2^{nd}$ toothed portion
246 rod
248 coupling ball
26 surgical instrument
260 shaft
262 $1^{st}$ toothed portion
264 $2^{nd}$ toothed portion
266 rod
268 coupling ball
28 bearing portion
30 bearing block
32 toothing arrangement
34 electromotor
36 motor pinion
38 electromotor
40 motor pinion
42 intermediate pinion
44 electromotor
46 motor pinion
48 operator pivot lever
50 receiving orifice
52 electromotor
54 motor pinion
56 electromotor
58 motor pinion
60 operator pivot lever
62 receiving orifice
64 toothed rod
66 electromotor
68 motor pinion
70 channel
72 channel
74 radial outlet
76 radial outlet
78 connection channel
80 connection channel
82 suction/rinsing connections
84 suction/ringing connections
86 space
88 space
90 union nut
92 key pad
94 printed circuit board

What is claimed is:

1. Multifunctional instrument for microinvasive surgery having an operator hand grip (10), a multi-lumen tube (14) attached to the operator hand grip, at least two guide channels (16, 18, 20) formed in parallel in the tube, and surgical instruments (22, 24, 26) which are displaceably and rotatably mounted in the guide channels and comprise a shaft (220, 240, 260), on whose distal end is disposed in each case a surgical working element, wherein the instruments (22, 24, 26) can be displaced between a non-operative position, in which the respective working element is retracted into the tube, and a working position, in which the respective working element projects on the distal end of the tube, characterized in that the instruments (22, 24, 26) can be displaced into and out of the working position by means of a motor, at least one of the instruments (22, 24, 26) can be rotated in its working position by means of a motor, and an electronic control is provided to control at least the motor-driven displacement movements and rotational movements, wherein the tube (14) comprises two guide channels (16, 18) having a first diameter and one guide channel (20) having a second diameter which is larger than the first diameter, wherein the tube (14) further comprises at least one additional channel (70,72) which serves as a suction or rinsing channel, and wherein the at least one additional channels (70, 72) is formed adjacent to the guide channel (18) having the larger diameter.

2. Multifunctional instrument as claimed in claim 1, characterised in that the multi-lumen tube (14) is rotatably mounted on the operator hand grip (10) and can be rotated by a motor, wherein the rotational movement can be controlled by means of the electronic control.

3. Operator hand grip as claimed in claim 1, characterised in that electromotors (34, 38, 44, 52, 56, 66) are disposed inside the operator hand grip (10) to provide the motor-driven drive.

4. Multifunctional instrument as claimed in claim 3, characterised in that the electromotors allocated to the instruments can be coupled selectively to the instrument (22, 24, 26), which is to be selected in each case, by way of coupling elements (40, 42, 46, 54, 58, 68) which are connected between the respective instrument and the allocated electromotor(s).

5. Multifunctional instrument as claimed in claim 4, characterised in that the selective coupling is accomplished by a relative movement between the instrument and the allocated electromotor(s) or allocated coupling element (s).

6. Multifunctional instrument as claimed in claim 5, characterised in that the electromotors are fixedly disposed in the operator hand grip (10) and the selective coupling is accomplished substantially by rotation of the tube (14).

7. Multifunctional instrument as claimed in claim 1, characterised in that a proximal end portion of the shaft (220, 240, 260) of each instrument (22, 24, 26) which when inserted into the tube (14) projects from the proximal end of the tube, comprises toothing arrangements (222, 242, 262; 224, 244, 264) for engagement with the motor-driven drive.

8. Multifunctional instrument as claimed in claim 7, characterised in that the shaft (220, 240, 260) at least of one of the instruments (16, 18, 20) comprises a first toothed portion (222, 242, 262) for displacing the instrument in the axial direction and comprises a second toothed portion (224, 244, 264) for rotating the instrument.

9. Multifunctional instrument as claimed in claim 7, characterised in that the shaft (220, 240, 260) at least of one of the instruments (22, 24, 26) comprises at its proximal end a coupling element (228, 248, 268) for engagement with an actuating element (48, 60) for manually actuating the instrument.

10. Multifunctional instrument as claimed in claim 1, characterised in that the tube (14) comprises guide channels (16, 18, 20) with a different diameter.

11. Multifunctional instrument as claimed in claim 1, characterised in that the tube (14) comprises at least three guide channels (16, 18, 20).

12. Multifunctional instrument as claimed in claim 1, characterised in that the first diameter is 3 mm +/−0.5 mm and the second diameter is 5 mm +/−0.5 mm.

13. Multifunctional instrument as claimed in claim 1, characterised in that the angular spacing between the two guide channels (16, 18) with the smaller diameter is 90° as seen in relation to the longitudinal middle axis of the tube (14), and the angular spacing between the guide channels (16, 18) with the small diameter and the guide channel (18) with the larger diameter is 135° in each case.

14. Multifunctional instrument as claimed in claim 1, characterised in that the tube (14) comprises two additional channels (70, 72).

15. Multifunctional instrument as claimed in claim 1, characterised in that the two additional channels (70, 72) each comprise an approximately triangular cross-section.

16. Multifunctional instrument as claimed in claim 1, characterised in that each of the additional channels (70, 72) comprises on the proximal end portion of the tube (14) an outlet (74, 76) which extends radially outwards and is connected to a suction/rinsing connection (82, 84).

17. Multifunctional instrument as claimed in claim 16, characterised in that in the contact region between the tube (14) and the component (30) of the operator hand grip (10) which surrounds the tube in a sealing manner in the region of the outlet(s), there is provided a space (86, 88) which is connected on the one hand to the outlet (74, 76) and on the other hand to the suction/rinsing connection (82, 84), extends in the circumferential direction of the tube and which is formed in such a manner that the fluid connection between the additional channel and the suction/rinsing connection remains intact even when the tube (14) is rotated relative to the component (30).

18. Multifunctional instrument as claimed in claim 1, characterised in that for the purpose of loading and unloading instruments (22, 24, 26) the tube (14) is releasably connected to the operator hand grip (10), in particular by way of a plug-in connection (28, 30) with a union nut (90).

19. Multifunctional instrument as claimed in claim 1, characterised in that at least two of the surgical instruments (22, 24) have a short working stroke with tactile feedback, e.g. scissors and clamp applicator, and can be actuated manually after having been displaced to their working position by means of a motor, and that at least one of the surgical instruments (26) having a long working stroke, e.g. clip applicator, can be actuated manually or by motor after having been displaced to its working position by means of a motor.

20. Multifunctional instrument as claimed in claim 1, characterised in that the commands for the control are input via actuating elements (92) disposed on the operator hand grip (10).

21. Multifunctional instrument as claimed in claim 1, characterised in that the control permits commands to be input by means of a voice-control facility.

22. Multifunctional instrument as claimed in claim 20, characterised in that the commands to be processed by the control include at least the following: move the instruments (22, 24, 26) to the non-operative position or the working position and/or rotate the instruments and/or rotate the tube.

23. Multifunctional instrument as claimed in claim 21, characterised in that the commands are input optionally by voice-control or via actuating elements (92).

\* \* \* \* \*